United States Patent [19]

Houghton et al.

[11] Patent Number: 4,693,966
[45] Date of Patent: Sep. 15, 1987

[54] HUMAN MONOCLONAL ANTIBODIES FROM LYMPHOCYTES OF PATIENTS WITH MALIGNANT MELANOMA

[75] Inventors: Alan N. Houghton; Hannah Brooks; Richard J. Cote, all of New York; Herbert F. Oettgen, New Canaan, Conn.; Lloyd J. Old, New York, N.Y.

[73] Assignee: Sloan-Kettering Institute for Cancer Research, New York, N.Y.

[21] Appl. No.: 474,618

[22] Filed: Mar. 11, 1983

[51] Int. Cl.$^4$ .................... G01N 33/577; C12N 5/00; C07K 15/04

[52] U.S. Cl. .......................................... 435/7; 435/68; 435/172.2; 435/240.27; 436/548; 436/813; 935/100; 935/110; 530/387

[58] Field of Search ............... 436/547, 548, 804, 813, 436/542, 536; 435/4, 7, 68, 70, 172.2, 240, 948; 935/89, 95, 96, 99, , 100, 104, 107, 108, 110; 260/112 R; 530/387

[56] References Cited

U.S. PATENT DOCUMENTS

| | | | |
|---|---|---|---|
| 4,434,230 | 2/1984 | Ritts | 435/240 |
| 4,444,887 | 4/1984 | Hoffmann | 435/240 |
| 4,451,570 | 5/1984 | Royston | 435/240 |
| 4,464,465 | 8/1984 | Lostrom | 435/68 |
| 4,472,371 | 9/1984 | Burchiel | 424/1.1 |

OTHER PUBLICATIONS

Marx, J. L., Science, vol. 229, pp. 455–456 (1985).
Schook, L. B. et al, *Lymphokines*, vol. 2, pp. 1–19, (1981), Academic Press, N.Y.
*Human Lymphokines*, Khan, A. et al, eds., Academic Press, N.Y. (1982), pp. 219–226, 343–350 and 699–718.
Schwaber, J., Exp. Cell. Res., vol. 93, pp. 343–354 (1975).
Levy, R. et al, Proc. Natl. Acad. Sci., U.S.A., vol. 75(5), pp. 2411–2415 (5–1978).
Zurawski, V. R. et al, Clin. Res., vol. 26(3), p. 558A (1978).
Sikora, K. et al, Blood, vol. 54(2), pp. 513–518 (8–1979).
Olsson, L. et al, Proc. Natl. Acad. Sci., U.S.A., vol. 77(9), pp. 5429–5431 (9–1980).
Croce, C. M. et al, Nature, vol. 288, pp. 488–489 (12–1980).
Sikora, K. et al, Br. J. Cancer, vol. 43, pp. 105–107 (1981).
Sikora, K. et al, The Lancet, 2, Jan. 2, 1982, pp. 11–14 (1–1982).
Karpas, A. et al, Science, vol. 216, pp. 997–999 (5–1982).
Astaldi, G. C. B. et al, J. Immunology, vol. 128(6), pp. 2539–2542 (1982).
Glimcher, L. H. et al, Nature, vol. 298, pp. 283–184 (7–1982).
Edwards, P. A. W. et al, Eur. J. Immunol., vol. 12, pp. 641–648 (8–1982).
Chiorazzi, N. et al, J. Exper. Med., vol. 156, pp. 930–935 (9–1982).
Sikora, K. et al, Nature, vol. 300, pp. 316–317 (11–1982).
Kozbor, D. et al, Proc. Natl. Acad. Sci., U.S.A., vol. 79, pp. 6651–6655 (11–1982).
Cahan, L. D. et al, Proc. Natl. Acad. Sci., U.S.A., vol. 79 (pp. 7629–7633, (12–1982).
Nilsson, K. et al, Clin. Exp. Immun., vol. 7, pp. 477ff, (1970).
Zurawski, V. R. et al, Science, vol. 199, pp. 1439ff, (1978).
Irie, R. F. et al, Br. J. Cancer, vol. 44, pp. 262–266 (1981), Chem. Abst. CA95(23): 201886d.

(List continued on next page.)

*Primary Examiner*—Charles F. Warren
*Assistant Examiner*—M. Moskowitz
*Attorney, Agent, or Firm*—John P. White

[57] ABSTRACT

Human monoclonal antibodies which specifically bind to antigens found on cell surfaces of renal, lung, and breast cancer cells, intracellular cytoskeletal antigens, nuclear antigens, and cytoplasmic reticular antigens are disclosed. The antibodies are the product of hybridoma cell lines, where the immortal cell line may be, e.g., a human cell line, or a murine cell line.

7 Claims, 6 Drawing Figures

OTHER PUBLICATIONS

Irie, R. F. et al, Proc. Natl. Acad. Sci., U.S.A., vol. 79, pp. 5666–5670 (1982), Biol. Abst. 75027566.

Steinitz, M. et al, Nature, vol. 269, pp. 420–422 (1977).

Koskimies, S., Scand. J. Immunology, vol. 11, pp. 73–77 (1980).

Nowinski, R. et al, Science, vol. 210, pp. 537–539 (1980).

Schlom, J. et al, Proc. Natl. Acad. Sci., U.S.A., vol. 77, pp. 6841–6845 (1980), Bio. Abst. 71053848.

Lane, H. C. et al, J. Exp. Med., vol. 155, pp. 333–338 (1982).

Handley, H. H. et al. (1982) in *Hybridomas in Cancer Diagnosis & Treatment,* Mitchell, M. S. et al, eds. (Raven, N.Y.), pp. 125–132.

Pukel, C. S. et al, J. Exp. Med., vol. 155, p. 1133 (1982).

O'Hare, M. J. et al, Prot. Biol. Fluids, Coll. 30, pp. 265–268 (1982).

FIG. 5

MELANOMA — 0 1+ 2+ 3+
- SK-MEL-13
- SK-MEL-23
- SK-MEL-28
- SK-MEL-29
- SK-MEL-30
- SK-MEL-31
- SK-MEL-37
- SK-MEL-64
- SK-MEL-93
- SK-MEL-110
- SK-MEL-122
- SK-MEL-127
- SK-MEL-131
- SK-MEL-158
- SK-MEL-166
- Me Wo

MALIGNANT GLIOMA
- SK-MG-1
- SK-MG-3
- SK-MG-4
- SK-MG-7
- SK-MG-12
- SK-MG-16
- CJ
- U138 MG
- U251 MG

NEUROBLASTOMA
- SK-NMC
- SK-NSH
- LAN-1

RENAL CANCER — 0 1+ 2+ 3+
- SK-RC-1
- SK-RC-6
- SK-RC-7
- SK-RC-9
- SK-RC-10
- SK-RC-11
- CoKi-2

BLADDER CANCER
- 639v
- 253j
- 486p

BREAST CANCER
- BT-20
- CAMA

OVARIAN CANCER
- SK-OV-3
- OV 2774

LUNG CANCER
- SK-LC-6
- SK-LC-13
- CoLu-1

COLON CANCER
- HT 29

NORMAL ADULT CELLS
- SKIN FIBROBLASTS
- KIDNEY NK-1
- MELANOCYTES

NORMAL FETAL CELLS
- SKIN FIBROBLASTS
- WI-38

MOUSE CELLS
- B16 MELANOMA
- 3T3
- METH A SARCOMA

HUMAN MONOCLONAL ANTIBODIES FROM LYMPHOCYTES OF PATIENTS WITH MALIGNANT MELANOMA

BACKGROUND

This present invention was wholly or partially made with funds provided by the National Cancer Institute, Department of Human Health and Services under Grant No. CA-1766 and CA-08748. Accordingly, the United States Government has certain rights in this invention.

This invention concerns hybridomas which produce human monoclonal antibodies recognizing surface antigens and intracellular components of human cells and a method for making such hybridomas. The human monoclonal antibodies are useful in diagnosis of diseases associated with cancers.

Defining the antigenic changes that accompany malignant transformation and detecting whether these changes elicit immune recognition in the host of origin are central concerns of tumor immunology. Serological approaches to these issues have been vastly strengthened with the advent of hybridoma technology (Köhler, G. and C. Milstein. 1975, *Nature (Lond.)* 256: 495). Monoclonal antibodies are providing much new information about the antigenic structure of experimental and human cancers, and hybridoma analysis promises to be of great value in dissecting the humoral immune response to tumor antigens in tumor-bearing animals and humans.

The problem with past efforts to resolve the question of tumor-related immune response in humans using conventional serology has had to do with the issue of specificity (Old, L. J. 1981, *Cancer Res.* 41: 361). With the exception of virus-related antigens on tumors such as Burkitt's lymphoma and hepatoma (Giraldo, G. and E. Beth. 1980, *The Role of Viruses in Human Cancer.* Vol. 1 (Elsevier/North-Holland, New York)), and HLA antigens and blood group antigens, the nature and significance of other classes of human cancer antigens detected by human antibody are unknown. To assess the frequency and specificity of antibodies reacting with surface antigens of human cancer cells, we have analyzed the autologous reactivity of sera from a series of patients with melanoma. astrocytoma, renal cancer and leukemia (Carey, T. E., T. Takahishi, L. A. Resnick, H. F. Oettgen and L. H. Old. 1976, *Proc. Natl. Acad. Sci., U.S.A.* 73: 3278; Shiku, H., T. Takahishi, H. F. Oettgen and L. H. Old. 1976, *J. Exp. Med.* 144: 873; Shiku, H., T. Takahishi, L. A. Resnick, H. F. Oettgen and L. H. Old. 1977, *J. Exp. Med.* 145: 784; Albino, A. P., K. O. Lloyd, A. N. Houghton, H. F. Oettgen, and L. H. Old, 1981, *J. Exp. Med.* 154: 1764; Pfreundschuch, M., H. Shiku, T. Takahishi, R. Ueda, J. Ransohoff, H. F. Oettgen, and L. H. Old. 1978, *Proc Natl. Acad. Sci., U.S.A.* 75 5122; Ueda, R., H. Shiku, M. Pfreundschuh, T. Takahishi, W. Whitmore, Jr., H. F. Oettgen, K. O. Llyod, and L. J. Old. 1979, *J. Exp. Med.* 150: 564; Garrett, T. J., T. Takahishi, B. D. Clarkson, and L. J. Old. 1977, *Proc. Natl Acad. Sci., U.S.A.* 74: 4578). Three classes of antigens detected by autologous antibody have been defined in this way. Class 1 antigens are restricted to autologous tumor cells, not being detected on any other cell type, normal or malignant. Class 2 antigens are shared antigens, found on a proportion of allogeneic tumors as well as on autologous tumors; recent evidence indicates that some Class 2 antigens are autoantigenic differentiation antigens, as they are detected on a restricted range of normal tissues (Watanabe, T., C. S. Pukel, H. Takeyama, K. O. Lloyd, H. Shiku, L. T. C. Li, L. R. Travassos, H. F. Oettgen, and L. J. Old. 1982, *J. Exp. Med.* 156: 1884.). Class 3 antigens are widely distributed on normal and malignant cultures; these broadly represented antigens have not been extensively analyzed. Whereas Class 3 reactivity is relatively common, antibodies to Class 1 and Class 2 antigens are found infrequently (10% of patients).

Techniques for the production of human monoclonal antibodies using hybridoma methodology have been used to extend these studies of humoral immune reactions of cancer patients.

In contrast to the success of hybridoma technology in the production of mouse and rat monoclonal antibodies, comparable studies with human antibody-producing hybrids have lagged behind. The general experience of many investigators has been that fusion with drug-marked human myeloma or lymphoblastoid cell lines resulted in few clones with growth potential.

SUMMARY

The present invention provides hybridomas producing human monoclonal antibodies and a method for forming such hybridomas.

The human monoclonal antibody producing hybridoma cell lines of the present invention were formed by fusing a human myeloma cell line, a mouse myeloma cell line or human lymphoblastoid cell line with human lymphocytes from normal individuals and from individuals having malignant melanoma. The lymphocytes were obtained from lymph node or tumor specimen of normal individuals having malignant melanoma. Peripheral blood lymphocytes from normal individuals or individuals having malignant melanoma were also used in the fusions.

Human monoclonal antibodies produced by these hybridoma cell lines recognize cell surface antigens or cytoplamic components of human cells and are useful for differentiating between normal and malignant cells.

DESCRIPTION

The present invention comprises human monoclonal antibodies produced by these hybridoma cell lines which produce human monoclonal antibodies which recognize cell surface antigens and cytoplasmic components. Among the antigens recognized by these monoclonal antibodies are the Ma4 cell surface antigenic system and nucleii, nucleoli and cytoskeletal elements in the cytoplasm. More particularly, human monoclonal antibodies recognizing cell surface antigens and cytoplasmic components are antibodies Ma4, M307, M311, M304, M305 and M311. A panel comprised of these has been formed.

The present invention comprises in addition a method for distinguishing between normal and tumor human cells comprising immunoassay of the Ma4 antigenic system with the antibody Ma4. Melanoma, renal and breast tumors may be detected by the method.

The antibodies of the present invention are useful in the diagnosis of diseases associated with various cancers. Thus, these may be used to assay human epithelial cells by immunoassay of the Ma4 intracellular antigen with human monoclonal antibodies of the present invention.

The assay of the present invention comprises contacting a tissue containing melanoma cells with the antibody recognizing melanoma cell antigens, preferably monoclonal antibodies to one or more surface cell antigens or cytoplasmic components and observing the antigenic reaction between said monoclonal antibody and said antigen. In a preferred embodiment of the present invention the tissue to be assayed is first excised and is then either freshly or after being frozen or embedded in paraffin by methods well-known in the art contacted with said monoclonal antibodies. In this embodiment said antibodies may be tagged with colored groups or color forming substances such as enzymes, preferably peroxidase and its substrates, with flourescent substances or with radioactive elements by which the location of the antibodies may be traced. Serological assay of excised tissue is also an embodiment of the present invention. Thus passive hemmaglutination, antibody inhibition assay, or glycolipid-mediated immune adherence assay may be used. Likewise anti-mouse immunoglobulin assay and Protein A assays may be employed.

In another preferred embodiment of the present invention, the tissue to be assayed comprises the intact body of an individual or a whole portion thereof, the antibody is administered to the individual, the antibody having been tagged with a radioactive or other energy-producing element, and the whole body or part thereof is scanned externally for localization of radioactivity at the site of tumor cells.

The method of the present invention also comprises treatment of tumors in a patient wherein the monoclonal antibody recognizing the cell antigen of melanoma cells, preferably the cell differentiation antigen, is administered to the patient in an amount effective to inhibit the growth or proliferation of tumor cells. In a preferred embodiment of this method the antibody is tagged with a potentially tissue destructive agent which causes destructive agents comprise enemotoxic agents, chemotherapeutic agents, radionucleides, toxins, complement activators and clotting activators.

The following examples are intended to illustrate this invention without limiting same in any manner especially with respect to substantially functional equivalents of hybridomas, monoclonal antibodies and cell lines described and claimed herein.

AVAILABILITY OF HUMAN MONOCLONAL ANTIBODIES

The cell lines disclosed in the present invention are deposition at the American Type Culture Collection, Bethesda, Md. and bear the following deposit numbers:

| HmAb | ATCC # |
| --- | --- |
| Ma4 | 8222 |
| M54 | 8234 |
| M304 | |
| M305 | |
| M307 | 8235 |
| M311 | 8236 |

Deposit is for the purpose of enabling disclosure only and is not intended to limit the concept of the present invention to the particular materials deposited.

BRIEF DESCRIPTION OF THE FIGURES

FIG. 5 shows intracellular antigens detected by IgM antibodies in supernatants of cultures derived from fusions of lymphocytes from lymph nodes of malenoma patients with LICR-2 (M304 and M305 antibodies) and SKO-007 (M307 and M311 antibodies). (A) M311 detects a nuclear antigen (target SK-MEL-63 melanoma cell line), magnification 1000×; (B) M307 detects a cytoskeletal structure (target cell WI-38 fetal fibroblasts), magnification 400×; (C) M305 detects a dense cytoplasmic network (target cell WI-38), magnification 200×; (D) M304 detects a cytoplasmic antigen expressed by cells of neuroectodermal origin (target cell SK-MEL-93 melanoma cell line), magnification 400×.

FIG. 6 shows the reactivity of M304 antibody with a panel of cultured cells using indirect immunofluorescence assays. Horizontal bars indicate intensity (0 to 3+) of immunofluorescence reactions.

PREPARATION OF HYBRIDOMAS

Myeloma/Lymphoblastoid Cell Lines

Figure 1:
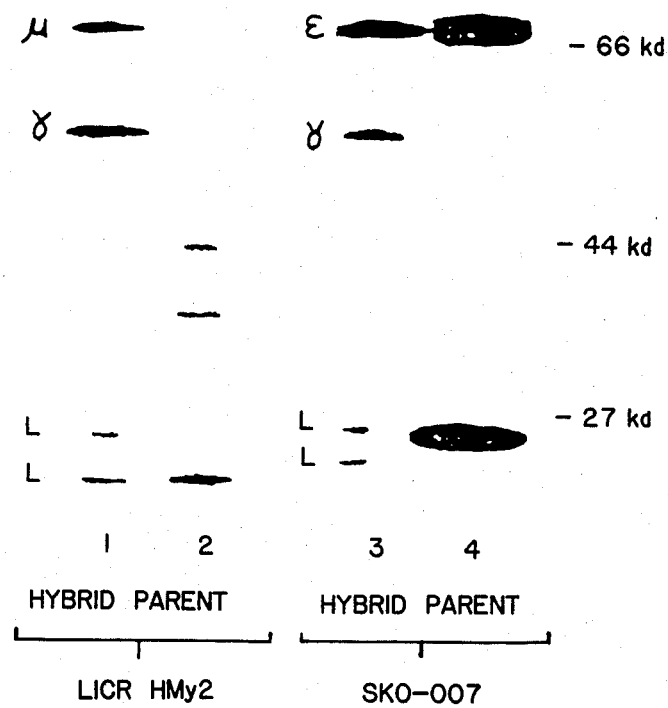
FIG. 1 depicts autoradiographs of [$^{35}$S] methionine-labeled immunoglobulins precipitated from culture supernatants of the Ma4 cell line (lane 1), LICR-2 human lymphoblastoid line (lane 2), Be3 cell line (lane 3) and SKO-007 human myeloma line (lane 4).

The human myeloma cell line SKO-007 (Olsson, L., and H. S. Kaplan. 1980, *Proc. Nat'l. Acad. Sci., U.S.A.* 77: 5429) was obtained from Becton-Dickinson Co., Sunnyvale, CA, and was rendered free of mycoplasma contamination by Dr. J. Fogh, Sloan-Kettering Institute. SKO-007 secretes ε heavy chain and λ light chain. The human LICR LON/HMy2 (abbreviated LICR-2) cell line (Edwards, P. A. W., C. M. Smith, A. M. Neville, and M. J. O'Hare. 1982, *Eur. J. Immunol.* 12: 641) was obtained from Drs. M. O'Hare, P. Edwards and M. Neville, London Branch of the Ludwig Institute for Cancer Research. This lymphoblastoid cell line secretes γ$_1$ heavy chain and κ light chain and expresses Epstein-Barr viris nuclear antigen (EBNA). The human lymphoblastoid cell line GM 4672, developed from the GM 1500 cell line by Croce et al. (Croce, C. A., A. Linnenbach, W. Hall, Z. Steplewski, and H. Koprowski. 1980, *Nature (Lond.)* 288: 488, was obtained from the Human Genetic Mutant Cell Repository, Institute of Medical Research, Camden, NJ. This cell line also expresses EBNA and secretes γ$_2$ heavy chain and λ light chain. The mouse myeloma cell line NS-1 (Köhler, G., C. S. Howe, and C. Milstein. 1976, *Eur. J. Immunol.* 6: 292), was obtained from Dr. U. Hammerling, Sloan-Kettering Institute. These cell lines were grown in RPMI 1640 medium (containing 2 mM glutamine, 1% nonessential amino acids, 100 U/ml penicillin and 1 g/ml 8-azaguanine. No growth occurred in medium containing $4 \times 10^{-7}$ aminopterin.

Fusion Procedure

Lymph node and tumor specimens from 33 patients with malignant melanoma were minced with fine scissors under sterile conditions. The resulting cell suspension was washed twice in RPMI 1640 medium and used as the source of lymphocytes for fusion. Peripheral blood lymphocytes from 25 melanoma patients were purified from heparinized venous blood by Ficoll-Hypaque (Pharmacia Fine Chemicals, Division of Pharmacia, Inc., Piscataway, NJ) gradient centrifugation. For further enrichment of B cells, T lymphocytes were removed by rosetting with neuraminidase-treated sheep erythrocytes and centrifugation through a Ficoll-Hypaque gradient.

Lymphocytes and myeloma/lymphoblastoid cells were fused at ratios of 1:1 or 2:1 for 3 min at 37° C. in 0.2 ml 41.5% (w/v) polyethylene glycol [molecular weight 4000 (J. T. Baker Chemical Co., Phillipsburg, NJ)] dissolved in 15% (v/v) dimethyl sulfoxide. Between $2 \times 10^6$ and $5 \times 10^7$ lymphocytes were used in each fusion experiment. After fusion, cells were washed and left overnight in RPMI 1640 medium containing 15% FBS (v/v). Optimum FBS was between to to 20% (v/v). The cells were then resuspended in RPMI 1640 medium containing 15% FBS, $2 \times 10^{-4}$M hypoxanthine, $4 \times 10^{-7}$M aminopterin, $3.2 \times 10^{-5}$M thymidine and $2 \times 10^{-5}$M 2-mercaptoethanol (HAT medium) and plated at $10^5$ cells per well into Costar 3696 well plates (Costar, Cambridge, MA) preceeded with feeder layers prepared from BALB/c or C57BL/6 splenocytes ($10^5$ cells/well) or peritoneal cells ($1-2 \times 10^4$ cells/well). Cells were maintained in HAT medium for a minimum of four week.

Cell Growth After Fusion of Lymphocytes with Myeloma/Lympho blastoid Cell Lines Results of fusions with LICR-2, SKO-007, GM 4672 and NS-1 are presented in Table 1. Wells containing clonal outgrowth appeared most frequently after fusion with the NS-1 mouse myeloma line. Lymphocyte source did not influence the frequency of clonal outgrowth in the case of NS-1 fusions; clones appeared with equal frequency after fusion with lymphocytes from lymph node or peripheral blood. Fusions with the three human myeloma/lymphoblastoid cell lines resulted in a 3 to 25 times lower frequency of growing clones. In the case of lymphocytes from lymph node, fusion with LICR-2 resulted in a higher frequency of clonal outgrowth than fusion with SKO-007 or GM 4672. Uniformly poor results were obtained in LICR-2 or SKO-007 fusions with peripheral blood as the source of lymphocytes (median<1 clone per $10^7$ lymphocytes fused). Enriching the B cell population of peripheral blood lymphocytes by depleting T cells prior to fusion with LICR-2, however, resulted in a higher frequency of growing clones. In three cases where a direct comparison of results with enriched B cells and unpurified peripheral blood lymphocytes was carried out, the frequency of clonal outgrowth was 5 to 20 times higher with the T cell-depleted population.

Immunoglobulin Production by Growing Clones

Supernatants from wells with growing cells were tested for human $\mu$, $\gamma$ or $\alpha$ heavy chain production. The LICR-2 line produced between 10 ng and 100 ng $\gamma$ chain per ml supernatant, although an occasional well (<10%) contained as high as 2 $\mu$g $\gamma$ chain/ml. GM 4672 produced 10 ng-1 $\mu$g/ml of IgG. Neither $\mu$, $\gamma$ or $\alpha$ heavy chains were detected in supernatants of SKO-007 or NS-1. After fusion, $\mu$, $\gamma$ (>200 ng/ml) or $\alpha$ heavy chains were found in 50-80% of wells (Table 1). The relative proportion of $\mu$, $\gamma$ or $\alpha$-positive wells varied from specimen to specimen, and no consistent pattern was observed in relation to source of lymphocytes or the myeloma/lymphoblastoid line used as fusion partner (Table 1). The levels of Ig production ranged from 0.3 $\mu$g-40 $\mu$g/ml. Once again, no apparent relation was found between the level of Ig secreted and the different fusion partners or sources of lymphocytes. Wells containing more than one Ig class were often encountered after fusions with LICR-2 and SKO-007. In most cases, wells with two Ig classes contained heavy chain and a second heavy chain class, either $\mu$ or $\alpha$. This could be due to the production of two heavy chains by the hybrid cells (in the case of LICR-2 or GM 4672 fusions), or to polyclonal outgrowth of Epstein-Barr virus (EBV)-transformed cells.

The stability of Ig production by cells derived from fusions with NS-1 and LICR-2 was examined by subculturing Ig+ wells using a limiting dilution technique. Cells from 77% (76/99) of Ig+ wells from LICR-2 fusions continued to produce Ig after one subculture (between 2-3 months after fusion), and 61% remained Ig+ after a second subculture (at 3-4 months). A lower percentage of mouse/human clones had persistent Ig production; 58% (43/74) of Ig+ wells from NS-1 fusions remained Ig+ after the first subculture (at 2 months after fusion), and 30% were Ig+ after the second subculture (at 3 months).

Screening of Immunoglobulin for Reactivity with Cell Surface Antigens

Supernatants of Ig+ wells were tested for reactivity with cell surface antigens by red cell rosetting assays using a panel of 20 cell lines, including 10 melanomas, 2 gliomas and 8 epithelial cancers (Table 2). Of 771 wells screened, positive reactions were observed with supernatants from 6 wells (0.8%). Efforts to isolate antibody secreting clones from these 6 wells resulted in the establishment of one cell line, designated Ma4, that continued to produce an IgM antibody to a surface antigen of human cells. The Ma4 line was derived from a fusion of LICR-2 with lymphocytes from a regional lymph node of a 35-year-old man with recurrent malignant melanoma. The line has been subcloned (1 cell/well) four times and has maintained stable production of IgM (5 $\mu$g/ml) and IgG (2 $\mu$g/ml) over a 12-month period. The Ma4 cell line is tetraploid by flow cytometry and contains only human chromosomes by karyotypic analysis. FIG. 1 shows that the Ma4 line secretes two distinct sets of heavy and light chains. Another Ig-secreting line derived from fusion of SKO-007 with lymphocytes from an axillary lymph node of a melanoma patient was cloned 2 times and has continued to produce IgG (without detectable reactivity) over a 5-month period. SDS-PAGE analysis shows that this line, designated Be3, also produced two distinct sets of light and heavy chains (FIG. 1).

Immunoglobulin Assays

Supernatants from wells containing growing clusters of cells were assayed for human $\mu$, $\gamma$ or $\alpha$ heavy chains by an enzyme-linked immunoassay. Costar 3696 96 well plates were precoated with human IgG (50 g/ml), IgA (50 g/ml), or igM (10 g/ml) (Cappel Laboratories, Cochranville, PA) overnight at 4° C. The precoated wells were washed with phosphate-buffered saline pH 7.5 (PBS) and incubated with gammaglobulin-free FBS (Gibco Laboratories, Grand Island, NY) for 30 min. Goat anti-human $\mu$, $\gamma$ or $\alpha$ heavy chain antibodies linked to alkaline phosphatase (Sigma Chemical Co., St. Louis, MO), diluted 1:100, were mixed [1:1 (v/v)] with test supernatants or with IgG, IgA or IgM standards diluted in RPMI 1640 medium containing 15% FBS (final concentrations of standards were 10 ng/ml, 100 ng/ml, 1 $\mu$g/ml, 10 $\mu$g/ml and 100 $\mu$g/ml) and incubated for 90 min. The mixtures were then transferred to precoated wells, incubated for 60 min, and washed with PBS. Alkaline phosphatase activity was detected using a p-nitrophenyldisodium phosphate substrate (Sigma Chemical Co.), with changes in optical density measured on an Artek Model 210 Reader (Artek Systems Corp., Farmingdale, NY). The assay detected $\leq 100$ ng/ml of $\mu$, $\gamma$ or $\alpha$ heavy chains and was specific for each Ig class over a range of $\leq 100$ ng/ml to $\geq 100$ $\mu$g/ml.

CHARACTERIZATION OF HUMAN MONOCLONAL ANTIBODIES FROM HYBRIDOMAS

Antibody Reactivity to Cell Surface and Intracellular Antigens

Supernatants from wells containing $\geq 200$ ng/ml Ig were screened for reactivity to cellular antigens using the following panel of human tumor cell lines: Melanomas (SK-MEL-13,19,23,28,29,37,93,147,165 and MeWO); Malignant gliomas (U251Mg, SK-MG-3); Epithelial cancers (SK-RC-7, SK-RC-9, BT-20, CAMA, 253J, HT29, OV2774 and Calu-1). To detect cell surface antigens, target cells were plated in Falcon 3034 plates and red cell rosetting assays for IgG [protein A (PA) assay] and IgM [immune adherence (IA) assay] were performed as previously described (Shiku, H., T. Takahishi, H. F. Oettgen and L. H. Old. 1976, *J. Exp. Med.* 144: 873; Pfreundschuh, M., H. Shiku, T. Takahishi, R. Ueda, J. Ransohoff, H. F. Oettgen, and L. H. Old. 1978, *Proc Natl. Acad. Sci., U.S.A.* 75 5122). IgA antibodies were detected by indicator cells prepared by conjugating purified anti-human IaA (Accurate Chemical and Scientific Corp., Westbury, NY) to human red blood cells with 0.01% chromium chloride. Absorption tests were performed according to previously described procedures (Carey, T. E., T. Takahaski, L. A. Resnick, H. F. Oettgen and L. J. Old. 1976, *Proc. Nat'l. Acad. Sci., U.S.A.* 73: 3278.). To detect intracellular antigens, supernatants were screened by indirect immunofluorescence tests. Target cells growing in Falcon 3034 plates were fixed with a 1:1 (v/v) methanol;acetone mixture for 5 min at room temperature. The cells were incubated with supernatant for 1 hr at room temperature, washed, and incubated with a 1:50 dilution of goat anti-human Ig conjugated to FITC (Cappel Laboratories, Inc.) for 45 min. Fluorescence was evaluated with a Leitz Dialux 20 microscope.

Chloroform:Methanol Extraction

Cells were extracted with chloroform:methanol by procedures described by Pukel, et al, *J. Exp. Med* 155: 1133 (1982). Antibody inhibition tests were carried out by mixing the cell extract with antibody containing supernatant (diluted two dilutions below the endpoint), incubating for 1 hr. at 20° C., and testing for residual antibody reactivity using SK-RC-9 target cells.

Radioimmunoprecipation Analysis of Secreted Immunoglobulins

Cells were cultured at $1 \times 10^6$ cells epr ml for 12 hrs in Eagle's minimum essential medium (lacking methionine), 1% FBS and 50 Ci[$^{35}$S] methionine (New England Nuclear, Boston, MA). Immunoglobulins in the culture fluid were precipitated with rabbit anti-human immunoglobulin antibodies (Accurate Chemical and Scientific Corp.) and *S. aureus* (Bethesda Research Laboratories, Bethesda, MD), and immunoprecipitates were analyzed by NaDodSo$_4$/polyacrylamide gel electrophoresis (SDS-PAGE) according to Laemmli (Laemmli, U.K. 1970, *Nature (Lond.)* 227: 680).

Definition of the Ma4 Antigen

Figure 2:
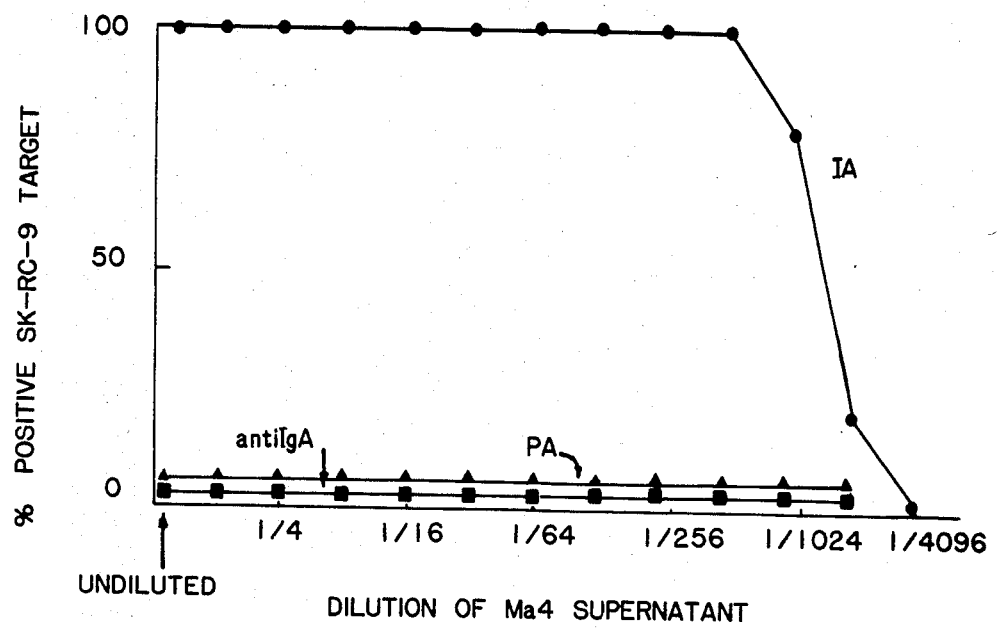
FIG. 2 shows reactivity of Ma4 culture supernatant with SK-RC-9 renal cancer cells as determined by three serological assays, i.e., Immunoadsorbence (IA), Protein A (PA), and Anti-IgA assays.
Figure 4:
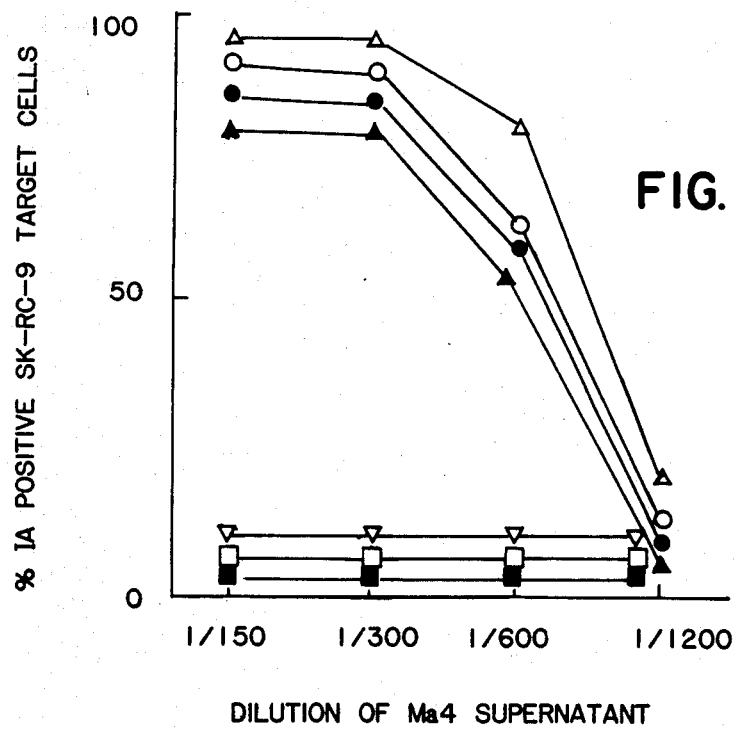
FIG. 4 shows absorption analysis of IA reactivity of Ma4 culture supernatants (diluted 1:150) for SK-RC-9 renal cancer cells.
Figure 3:
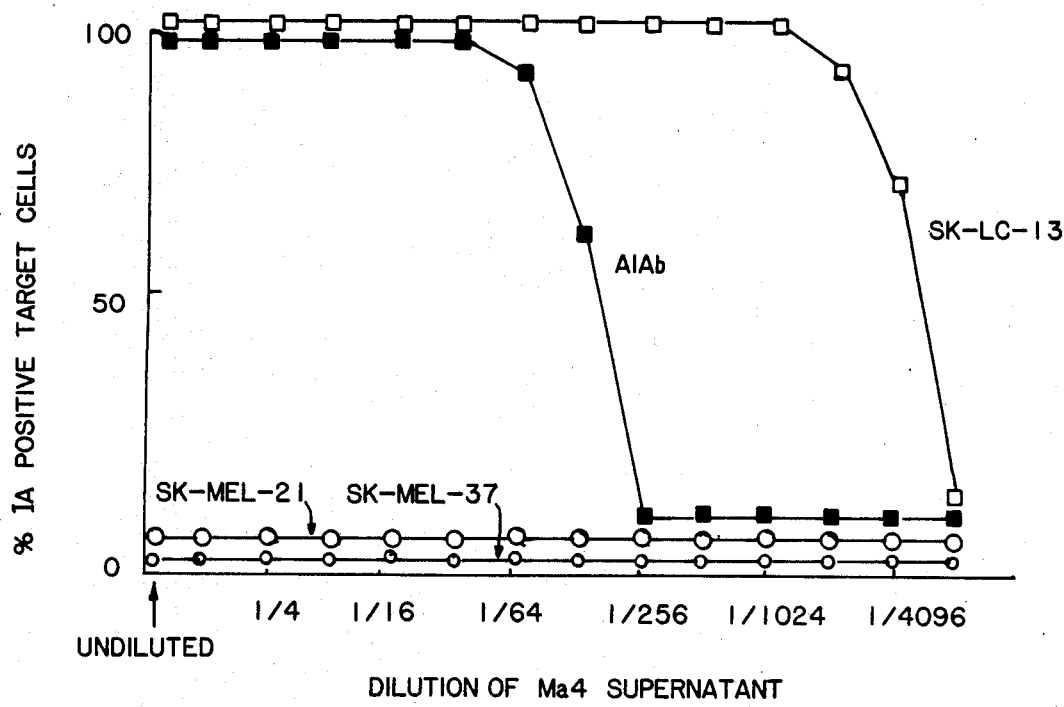
FIG. 3 shows the reactivity via immunoadsorbence assay of Ma4 culture supernatants with four human cancer cell lines, i.e. SK-LC-13 (lung cancer), AlAb (breast cancer), SK-MEL-21 and SK-MEL-37 (melanomas).

Supernatants from cultures of the Ma4 cell line were found to be highly reactive with SK-RC-9 (an established cell line derived from human renal cancer) (FIG. 2). Reactivity was detected by IA assays for IgM antibody, but not by assays detecting IgA or IgG antibodies. [Serum from the patient providing lymphocytes used in the construction of the Ma4 cell line was unreactive (titer 1:2) with SK-RC-9 target cells by IA assay.] FIG. 3 illustrates IA tests with Ma4 supernatant on 4 other established human cell lines; reactions were seen with SK-LC-13, a cell line derived from lung cancer, and AlAb, a cell line derived from breast cancer, but not with 2 melanoma cell lines. FIG. 4 demonstrates analysis of Ma4 antibody reactivity by absorption analysis using a panel of 81 different cell types.

The antigen detected by Ma4 antibody was found to be heat stable (100° C. for 10 min) and resistant to treatment with trypsin and proteinase K. Chloroform:methanol extracts of the Ma4-positive cell line SK-RC-9 completely inhibited Ma4 antibody reactivity. Extracts from Ma4-negative cell lines (253J and BT-20) had no inhibitory activity.

Screening of Immunoglobulin for Reactivity to Intracellular Antigens

Supernatants from the 771 Ig+ wells that were tested for reactivity to cell surface antigens were also tested for reactivity to intracellular antigens by indirect immunofluorescence assays. Twenty-four (4%) wells contained antibodies reacting with nuclei, nucleoli, cytoskeletal elements or other cytoplasmic components (Table 2). Cell lines secreting IgM antibody were derived from 4 of these wells and antibody production by these lines has remained stable over a 4 to 7 months observation period. Antibodies M307 and M311 came from fusions of lymph node lymphocytes with SKO-007 and antibodies M304 and M305 from fusions of lymph node lymphocytes with LICR-2. Antibody M311 showed granular staining of the nucleus. Antibodies M305 and M307 reacted with cytoplasmic components in a wide range of cultured cell types; M307 stained a cytoskeletal network and staining with M305 showed a dense reticular pattern. Antibody M304 also reacted with cytoplasmic components, but in the case of this antibody reactions were restricted to cell lines of neuroectodermal origin (FIG. 6). Astrocytomas (9 of 9 tested), melanomas (9 of 16 tested), neuroblastomas (1 of 3 tested) and normal melanocytes reacted with antibody M304. No reactions were observed with 18 epithelial cancers or with cultures of normal kidney or fibroblasts.

In an attempt to analyze the humoral immune reactions of patients with malignant melanoma by hybridoma methodology, lymphocytes from regional lymph nodes, peripheral blood and tumor infiltrates, 157 lymphocytes were fused with any of SKO-007 (human myeloma line), LICR LON/HMy2 (LICR-2) and GM 4672 (human lymphoblastoid lines), or NS-1 (mouse myeloma line). Fusion of lymph node lymphocytes with NS-1 resulted in a 3 to 4 times higher frequency than fusion with SKO-007 or GM 4672. In the case of peripheral blood lymphocytes, fusion with NS-1 gave 25 times higher frequency of clones than fusion with LICR-2 or SKO-007. Production of human $\mu$, $\gamma$ or $\alpha$ heavy chains was detected in 50–80% of wells containing growing clones, and the levels of immunoglobulin ranged from 0.3 $\mu$g–40 $\mu$g/ml. NS-1 derived clones could be easily subcultured, while LICR-2 and SKO-007 clones grew more slowly on subculturing. In this study, Ig-secretion appeared to be more stable property of LICR-2-derived clones than NS-1-derived clones. A 771 Ig-secreting cultures for antibody to cell surface or intracellular antigens. Reactivity with cell surface antigens was found infrequently (6 cultures), whereas reactivity with intracellular antigens was more common (27 cultures). A new cell surface antigen with properties of a glycolipid was defined with an IgM monoclonal antibody secreted by a tetraploid cell derived from a fusion of LICR-2 with lymphocytes from the axillary lymph node of a patient with melanoma. The hybrid cell line has been subcloned 4 times and secretes 5 $\mu$g IgM/ml. The antigen detected by this IgM antibody was found on 5/23 melanoma cell lines and 12/30 epithelial cancer cell lines. No ractions were found with 11 cultures derived from normal cells. Stable cell lines secreting human antibody detecting nuclei, nucleoli, cytoskeletal elements or other cytoplasmic components were also isolated in this study. One antibody detected an intracellular antigen that is restricted to cells of neuroectodermal derivation. Using these methods for isolating and analyzing human monoclonal antibody, it should now be possible to define the repertoire of the humoral immune response to melanoma.

TABLE I

FUSION OF LYMPHOCYTES FROM MELANOMA PATIENTS WITH LICR-2, SK0-007, GM 4672 OR NS-1 MYELOMA/LYMPHOBLASTOID CELL LINES

| FUSION PARTNER | SOURCE OF LYMPHOCYTES | NO. OF FUSIONS | NO. OF WELLS WITH GROWING CLONES* | NO. OF WELLS WITH CLONES PER $10^7$ LYMPHOCYTES FUZED | | NO. (%) OF Ig+ WELLS+ | NO. (%) OF Ig+ WELLS PRODUCING Ig HEAVY CHAINS | | |
|---|---|---|---|---|---|---|---|---|---|
| | | | | Median | Range | | $\mu$ | $\gamma$ | $\alpha$ |
| LICR-2 | Lymph Node | 31 | 470 | 8.3 | 0–100 | 373 (79%) | 189 (51%) | 280 (75%) | 72 (19%) |
| | Tumor Infiltrate | 5 | 71 | 8.3 | 0–50 | 65 (91%) | 37 (57%) | 25 (38%) | 33 (51%) |
| | Peripheral Blood Lymphocytes | 31 | 45 | <1.0 | 0–25 | 31 (69%) | 7 (23%) | 24 (77%) | 3 10%) |
| | Peripheral Blood B Cells | 10 | 12 | 6.1 | 0–25 | 9 (75%) | 4 (33%) | 7 (77%) | 0 |
| SK0-007 | Lymph Node | 22 | 50 | 1.0 | 0–5 | 39 (78%) | 19 (49%) | 33 (85%) | 14 (36%) |
| | Tumor Infiltrate | 2 | 1 | — | 0–1 | 0 | — | — | — |
| | Peripheral Blood Lymphocytes | 27 | 61 | <1.0 | 0–33 | 52 (69%) | 16 (31%) | 38 (73%) | 12 (23%) |
| | Peripheral Blood B Cell | 5 | 14 | 2.0 | 0–10 | 8 (57%) | 4 (50%) | 4 (50%) | 1 (13%) |
| GM 4672 | Lymph Node | 8 | 8 | 1.0 | 0–1 | 8 (100%) | 2 (25%) | 8 (100%) | 0 |
| NS-1 | Lymph Node | 11 | 278 | 22.2 | 0–100 | 156 (56%) | 68 (44%) | 93 (60%) | 23 (15%) |
| | Peripheral Blood Lymphocytes | 6 | 66 | 25.0 | 0–50 | 30 (45%) | 26 (87%) | 10 (33%) | 5 (17%) |

*Wells with continuing outgrowth more than 2 weeks after fusion. Growing clones derived from fusions with LICR-2, SK0-007 and GM 4672 appeared between 3–8 weeks after fusion; growing clones from fusions with NS-1 appeared between 2–6 weeks.
+ Wells with clonal outgrowth containing >200 ng/ml $\mu$, $\gamma$ or $\alpha$ heavy chain in the supernatant.

panel of 20 human cancer cell lines was used to screen

TABLE 2

SCREENING OF SUPERNATANTS FOR ANTIBODY REACTIVITY WITH CELL SURFACE ANTIGENS AND INTRACELLULAR ANTIGENS

| SOURCE OF LYMPHOCYTES | MYELOMA/ LYMPHOBLASTOID CELL LINES | NO. OF Ig+WELLS SCREENED* | CELL SURFACE ANTIGENS | | | INTRACELLULAR ANTIGENS | | |
|---|---|---|---|---|---|---|---|---|
| | | | IA | PA | ANTI-IgA | NUCLEAR | NUCLEOLAR | CYTOPLASM |
| Lymph Node and Tumor Infiltrates | LICR-2 | 438 | 2 | 1 | 0 | 2 | 1 | 8 |
| | GM 4672 | 8 | 0 | 0 | 0 | 0 | 0 | 0 |
| | SK0-007 | 39 | 0 | 0 | 0 | 0 | 1 | 7 |
| | NS-1 | 156 | 1 | 1 | 0 | 0 | 0 | 6 |
| Peripheral Blood | LICR-2 | 40 | 1 | 0 | 0 | 0 | 1 | 1 |
| | SK0-007 | 60 | 0 | 0 | 0 | 0 | 0 | 0 |
| | NS-1 | 30 | 0 | 0 | 0 | 0 | 0 | 0 |
| TOTAL: | | 771 | 4 | 2 | 0 | 2 | 3 | 22 |

* Panel of cell lines tested: Melanomas (SK-MEL-13,19,23,28,29,37,93,147,165 and MeWo); Malignant gliomas (U251MG, SK-MG-3); Epithelial Cancers (SK-RC-7, SK-RC-9, BT-20, CAMA, 253J, HT29, OV2774 and Calu-1).

TABLE 3

RESULTS OF DIRECT TESTS AND ABSORPTION ANALYSIS OF IA REACTIVITY OF Ma4 CULTURE SUPERNATANT. DEFINITION OF THE Ma4 ANTIGEN SYSTEM

| Cell Line | Titer* | Absorption | Cell Line | Titer | Absorption |
|---|---|---|---|---|---|
| RENAL CANCER | | | MELANOMA | | |
| SK-RC-4 | — | — | SK-MEL-37 (BD) | — | — |
| SK-RC-7 | — | — | SK-MEL-41 (BH) | — | — |
| SK-RC-9 | 1:1280 | + | SK-MEL-90 (DO) | — | — |
| SK-RC-28 | — | + | SK-MEL-93 (DX-1) | — | — |
| SK-RC-38 | — | — | SK-MEL-93 (DX-2) | — | — |
| BLADDER CANCER | | | SK-MEL-110 (EI) | 1:32 | + |
| T-24 | 1:64 | + | SK-MEL-113 (EL) | — | — |
| 639v | — | — | SK-MEL-118 (EQ) | — | — |
| Scb | — | + | SK-MEL-127 (EZ) | — | — |
| RT-4 | — | — | SK-MEL-131 (FD) | — | — |
| 253J | — | — | SK-MEL-147 (FT) | — | + |
| 647v | — | — | SK-MEL-165 (GL) | — | — |
| TCC-SUP | — | — | MALIGNANT GLIOMA | | |
| BREAST CANCER | | | SK-MG-1 | 1:2 | + |
| ICF-7 | — | — | SK-MG-3 | — | — |
| CAMA | — | + | SK-MG-9 | — | — |
| BT-20 | — | — | SK-MG-10 | — | — |
| AlAb | 1:128 | + | SK-MG-13 | — | — |
| LUNG CANCER | | | J251 MG | — | — |
| Calu-1 | — | — | J373 MG | 1:15 | + |
| SK-LC-6 | 1:4 | + | T98 | — | — |
| SK-LC-8 | — | — | HEMATOPOIETIC CELLS | | |
| SK-LC-13 | 1:4000 | + | SK-LY-16 | — | |
| OVARIAN, CERVICAL AND UTERINE CANCER | | | SK-LY-18 | | |
| | | | EBV-TRANSFORMED B CELLS | | |
| ME-180 | — | — | AH | | — |
| OV-2774 | 1:256 | + | AV | | — |
| SK-OV-3 | — | — | AZ | | — |
| Colo 316 | — | — | DX | | — |
| ROAC | — | — | EI | | — |
| SK-UT-1 | — | — | ADULT FIBROBLASTS | | |
| COLON CANCER | | | AS | | |
| HT-29 | — | + | BG | | — |
| SW 620 | — | — | DX | | — |
| SW 480 | 1:2 | + | RC-9 | | — |
| SW 1222 | — | + | FETAL CELL LINES | | |
| MELANOMA | | | WI-38 | | |
| SK-MEL-13 (AH) | — | — | F-5 Brain | — | — |
| SK-MEL-19 (AL) | — | — | Flow 5000 | — | — |
| SK-MEL-21 (AN) | — | — | NORMAL KIDNEY | | |
| SK-MEL-23 (AP) | — | + | NK-1 | — | — |
| SK-MEL-26 (AS) | — | — | NK-2 | — | — |
| MeWo | — | — | MELANOCYTES | | |
| SK-MEL-28 (AU) | — | — | FS 751 | — | |
| SK-MEL-29 (AV) | — | + | FS 752 | | |
| SK-MEL-30 (AW) | — | — | RED BLOOD CELLS | | |
| SK-MEL-31 (AX) | — | — | A, B, AB, O | | |
| SK-MEL-33 (AZ) | 1:128 | + | Sheep erythrocytes | | |

Footnotes to Table 3
*Titer: (—) indicates no reaction in direct tests of undiluted culture supernatants.
 Absorption: Culture supernatant (diluted 1:64 to 1:256 according to endpoint) was absorbed with the indicated cell type and tested for residual activity to SK-RC-9 renal cancer target cells.

What is claimed is:

1. Human monoclonal antibody Ma4 (HB8222), wherein said monoclonal antibody is IgM and specifically binds to an epitope of a glycolipid antigen, said antigen found on the cell surface of human renal, lung, and breast cancer cells.

2. Human monoclonal antibody M54 (HB 8234) which specifically binds to an antigen characteristic of human cells of epithelial origin.

3. Human monoclonal antibody M307 (HB 8235), wherein said monoclonal antibody is IgM and specifically binds to an intracellular cytoskeletal antigen of human cells.

4. Human monoclonal antibody M311 (HB 9054), wherein said monoclonal antibody specifically binds to a nuclear antigen of human cells.

5. A panel of human monoclonal antibodies, wherein said panel is used to characterize human cell antigens and said panel consists of at least one of the antibodies Ma4 (HB 8222), M54 (HB 8234), M307 (HB 8235) and M311 (HB 9054).

6. Hybridoma cell lines which produce monoclonal antibodies wherein said cell lines are selected from the group consisting of ATCC HB 8222, ATCC HB 8234, ATCC HB 8235, and ATCC HB 8236.

7. A method of characterizing human cell samples comprising contacting a sample of human cells with a panel of monoclonal antibodies which consists of at least two monoclonal antibodies selected from the group consisting of Ma4 (HB 8222), M54 (HB 8234), M307 (HB 8235) and M311 (HB 9054) under conditions favoring formation of complexes between said monoclonal antibodies and antigens of cells in said sample to which said monoclonal antibodies specifically bind, and determining the presence of said monoclonal antibody-antigen complexes.

* * * * *